United States Patent
Ahmed et al.

(10) Patent No.: US 10,362,994 B2
(45) Date of Patent: Jul. 30, 2019

(54) BIO-SENSING DEVICE WITH AMBIENT LIGHT CANCELLATION

(71) Applicant: TEXAS INSTRUMENTS INCORPORATED, Dallas, TX (US)

(72) Inventors: Hussam Ahmed, Calicut (IN); Jagannathan Venkataraman, Bangalore (IN); Sandeep Kesrimal Oswal, Bangalore (IN); Antoine Lourdes Praveen Aroul, Dallas, TX (US); Hari Babu Tippana, Andhra Pradesh (IN); Anand Hariraj Udupa, Bangalore (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 476 days.

(21) Appl. No.: 15/298,764

(22) Filed: Oct. 20, 2016

(65) Prior Publication Data

US 2017/0245803 A1  Aug. 31, 2017

Related U.S. Application Data

(60) Provisional application No. 62/301,326, filed on Feb. 29, 2016.

(51) Int. Cl.
*A61B 5/1455* (2006.01)
*A61B 5/00* (2006.01)
(Continued)

(52) U.S. Cl.
CPC ........ *A61B 5/7225* (2013.01); *A61B 5/02416* (2013.01); *A61B 5/681* (2013.01); *A61B 5/7203* (2013.01); *A61B 2560/0247* (2013.01)

(58) Field of Classification Search
CPC ... A61B 5/1455; A61B 5/14551; A61B 5/721; A61B 5/7225; A61B 5/681; A61B 5/0205
See application file for complete search history.

(56) References Cited

U.S. PATENT DOCUMENTS

| 8,283,620 B2 | 10/2012 | Raynor et al. |
| 2004/0010192 A1 | 1/2004 | Benaron et al. |
| (Continued) | | |

FOREIGN PATENT DOCUMENTS

WO  2015164774  10/2015

OTHER PUBLICATIONS

Supplementary European Search Report from corresponding EP Application No. EP17760635, dated Jan. 17, 2019 (3 pages).
(Continued)

*Primary Examiner* — Eric F Winakur
(74) *Attorney, Agent, or Firm* — John R. Pessetto; Charles A. Brill; Frank D. Cimino

(57) ABSTRACT

A bio-sensing device (and method) calibrates a time period used to make bio-physical measurements. The device initiates a light source sense phase followed by a first ambient sense phase and a second ambient sense phase. In the light source sense phase, the device is configured to receive a digital value indicative of current through a photodetector while the light source circuit is enabled and in each of the first and second ambient sense phases, the device is configured to receive digital values while the light source circuit is disabled. The device iteratively varies the time period between the phases until the digital value received during the first ambient sense phase is within a threshold of the digital value received during the second ambient sense phase. It then applies the same time separation between the
(Continued)

light source sense phase and the ambient phase thereby equalizing the magnitude of the ambient light in the two phases.

19 Claims, 3 Drawing Sheets

(51) Int. Cl.
*A61B 5/0205* (2006.01)
*A61B 5/024* (2006.01)

(56) References Cited

U.S. PATENT DOCUMENTS

| | | |
|---|---|---|
| 2007/0203405 A1 | 8/2007 | Shimomura |
| 2008/0208016 A1 | 8/2008 | Hughes et al. |
| 2010/0087718 A1* | 4/2010 | Gonopolskiy ..... A61B 5/14551 600/323 |
| 2010/0268056 A1 | 10/2010 | Picard et al. |
| 2015/0173631 A1 | 6/2015 | Richards et al. |

OTHER PUBLICATIONS

International Search Report and Written Opinion, PCT/US 2017/019994, dated Jun. 29, 2017 (6 pages).

* cited by examiner

BIO-SENSING DEVICE WITH AMBIENT LIGHT CANCELLATION

CROSS-REFERENCE TO RELATED APPLICATIONS

The present application claims priority to U.S. Provisional Patent Application No. 62/301,326, filed Feb. 29, 2016, titled "Cancelling Spurious Tones From Ambient Light Flicker In Optical Heart Rate Monitoring," which is hereby incorporated herein by reference in its entirety.

BACKGROUND

Some types of bio-sensing devices include a photo diode that generates light and a photo detector that senses the light reflected off a person's body. From the reflected light, the device can determine a biophysical property such as heart rate. Some bio-sensing devices are provided in the form of wrist watches that measure heart rate.

BRIEF DESCRIPTION OF THE DRAWINGS

For a detailed description of various examples, reference will now be made to the accompanying drawings in which.

DETAILED DESCRIPTION

Figure 1:
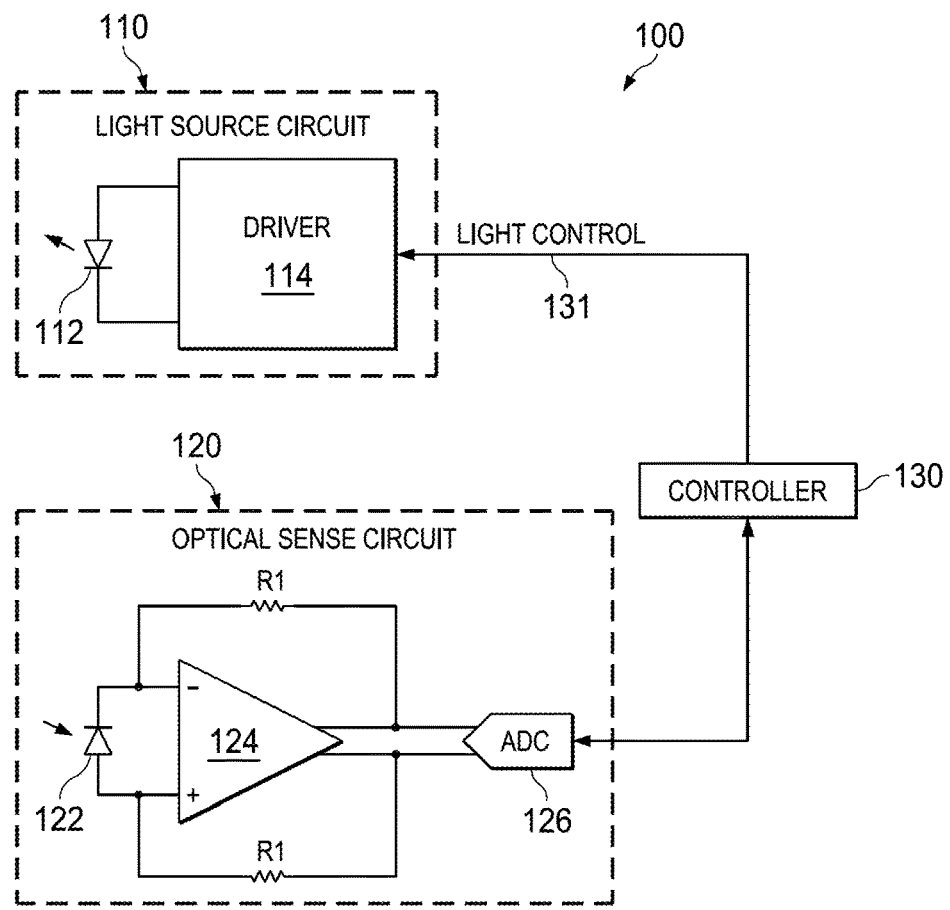
FIG. 1 shows an embodiment of an optical bio-sensing device in accordance with various examples.

An optical-based bio-sensing device is described herein that includes a light source and a photodetector and takes a reading from the photodetector with the light source enabled during a light source sense phase and then again during an ambient sense phase with the light source disabled. By subtracting the ambient light measured during the ambient sense phase from the light measured during the light source sense phase (which includes both reflected light at a suitable wavelength from the light source off the person as well as ambient light), any of a variety of biophysical parameters such as heart rate can be computed. In some embodiments, the optical-based bio-sensing device is in the form of a wrist-worn watch.

A controller in the bio-sensing device can assert a signal to turn the light source on and off. The controller disables (turns off) the light source during the ambient sense phases, and enables (turns on) the light source during the light source sense phases. During the ambient sense phases, the only light detected by the photodetector, in some examples, may be ambient light, and not light from the light source. In some cases, ambient light (e.g., light from a fluorescent light bulb) is periodic, and the frequency is such that the ambient phase in which ambient light is measured should closely follow the light source phase to ensure that the measurement of ambient light closely approximates the amount of ambient light that was present during the light source phase. However, closely spaced light source and ambient sense phases may require the device to have relatively high signal bandwidth which would result in a higher noise bandwidth and low signal-to-noise (SNR) ratio.

In accordance with the disclosed embodiments, the controller compares the sensed light signal magnitude during back-to-back ambient sense phases and iteratively varies the timing between such back-to-back ambient sense phases to determine the periodicity (e.g., period or frequency) of the ambient light signal. Approximately equal back-to-back ambient measurements indicate that the back-to-back ambient phases are aligned to the periodicity (e.g., period or frequency) of the ambient light signal itself. This timing separation is then set between the light source sense phase and the ambient phase to measure the relevant biophysical parameter. For example, during a determination of heart rate, the bio-sensing device's controller initiates a light source sense phase and then initiates an ambient sense phase at either the periodicity of, or an integer multiple (2, 3, 4, . . . ) of the periodicity of the ambient light signal. That is, the controller may initiate the ambient sense phase such that the interval between the light source sense phase and the ambient sense phase corresponds to either a period or an integer multiple of the period of the ambient light signal. The measured ambient signal is subtracted from the measured signal during the light source sense phase, and the heart rate is computed from the resulting difference. By ensuring the ambient sense phase is spaced from the light source sense phase at approximately an integer multiple of the period of the ambient light signal, the strength of the ambient signal in the two phases is more or less equal. As a result, the device is able to more fully remove the magnitude of the ambient light from the light measured during the light source sense phase.

FIG. 1 shows an example of bio-sensing device 100 in accordance with various embodiments. The device includes a light source circuit 110, an optical sense circuit 120, and a controller 130. In some embodiments, the controller may be any type of processor capable of executing program instructions (e.g., firmware). The instructions may be stored in memory internal to the processor or otherwise accessible to the processor. In other embodiments, the controller is a discrete circuit pre-configured to perform the operations described herein.

The light source circuit 110 includes a light emitting diode (LED) 112 (or other type of light source) coupled to a driver 114. The driver 114 produces a sufficient voltage and/or current to drive current through the LED 112 to produce light. In some embodiments, the LED is an infrared LED, but in general, the LED produces light at wavelength suitable for the intended purpose of the bio-sensing device 100, be it to measure heart rate, peripheral oxygen saturation value, pulse transit time, etc. The driver receives a LIGHT_CONTROL signal 131 from the controller 130. The LIGHT_CONTROL signal 131 can be asserted to either of two logic states to enable and disable the light source circuit 110, or at least cause the LED 112 to be turned on or turned off. For a light source sense phase, the controller 130 asserts the LIGHT_CONTROL signal 131 to a logic state that causes the driver 114 to turn on the LED 112. For an ambient sense phase, the controller 130 asserts the LIGHT_CON- TROL signal 131 to the opposite logic state that causes the driver 114 to turn off the LED 112.

The optical sense circuit 120 in the example of FIG. 1 includes a photo diode 122 (or photo transistor), a transimpedance amplifier 124, and an analog-to-digital converter (ADC) 126. One or more feedback resistors R1 may be included as well to set the gain of the transimpedance amplifier 124 to a desired level. Incident light on the photo detector 122 (which may be light generated by the LED 112 and reflected off a person's wrist) causes the photo detector 122 to generate a current proportional to the magnitude of the incident light. The transimpedance amplifier 124 converts the current to a voltage. The ADC 126 then converts the voltage generated by the transimpedance amplifier 124 to a digital value.

The controller 130 can command the ADC to generate a digital value (i.e., convert the analog voltage from the transimpedance amplifier 124 to a digital value) and provide the digital value to the controller 130. Alternatively, the ADC 126 may continuously digitize the analog voltage from the transimpedance amplifier 124, and the controller 130 reads the current digital value when needed. Controller 130 and/or bio-sensing device 100 may implement one or more of the ambient light cancellation techniques described in this disclosure.

Figure 2:
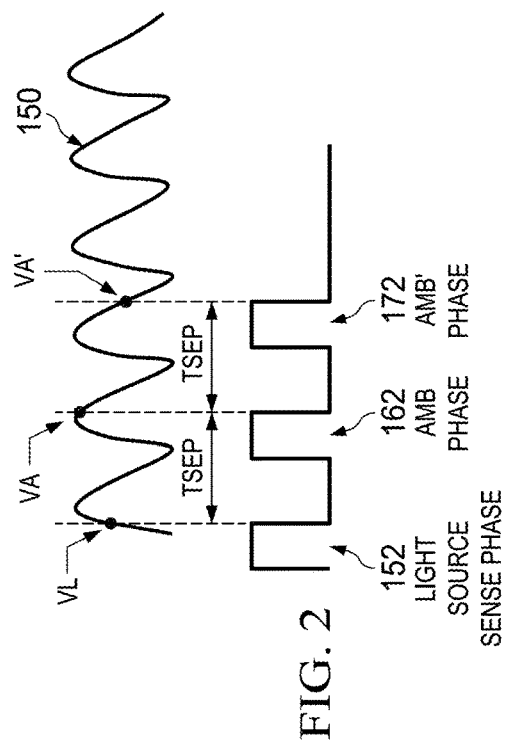
FIG. 2 shows an example of light sensing phases in which the phases are not aligned to the periodicity of the ambient light signal.

FIG. 2 shows an example of a periodic ambient light signal 150. Also shown are a light source sense phase 152, a first ambient sense phase 162 (AMB), and a second ambient sense phase 172 (AMB'). In each of these phases, the controller receives a digital value from the ADC 124. During the light source sense phase, the digital value read from the ADC is a signal from the photo diode that was sampled (e.g., converted to a voltage and digitized) while the LED 112 was enabled (on). In the example of FIG. 2, the digital value is generated and read at the end of the light source sense phase, but alternatively could be obtained any time during the light source sense phase. The digital value represents the measured light value and is denoted as VL. At a time period later (denoted as tsep), the controller 130 performs the first ambient sense phase 162 and reads another digital value from the optical sense circuit 120 this time with the LED 112 disabled (off). The measured value is denoted as VA to signify the measured light signal during an ambient sense phase. The controller implements the second ambient sense phase 172 after a tsep time period following the first ambient sense phase 162. The measured value during the second ambient sense phase is denoted as VA'. As such, the three measured light signal values—VL, VA and VA'—are measured with a timing of tsep between each measurement.

As can be seen in FIG. 2, the value of tsep is not aligned to the periodicity (or period) of the ambient light signal 150 and, as a result the magnitude of VA is significantly different the magnitude of VA'. Further, because the ambient sense phase is not executed an integer multiple of ambient signal cycles after the light source sense phase, the magnitude of the measured ambient signal (VA) is not likely to sufficiently approximate the magnitude of the ambient light signal incident on the photodetector 122 during the light source sense phase 152. Any resulting computation of heart rate or other biophysical parameter may not be sufficiently accurate. For example, tones present in the ambient light can also be present in the subtracted value (between the light source sense phase and the ambient phase) and can be mistakenly determined as the heart rate.

Figure 3:
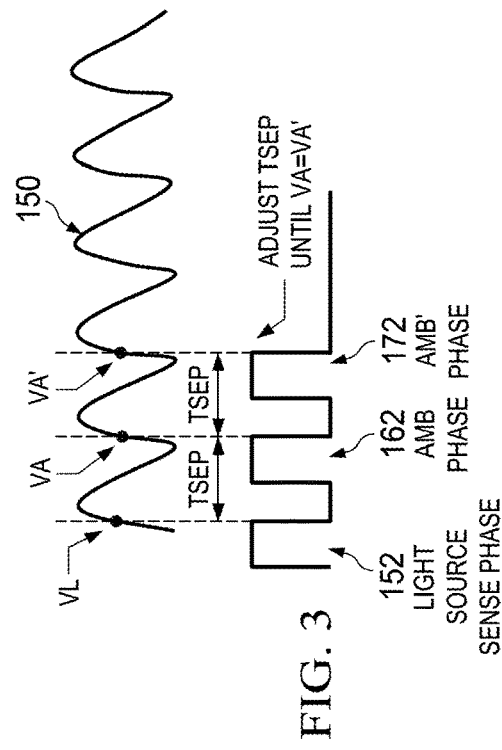
FIG. 3 shows an example of light sensing phases in which the phases are aligned to the periodicity of the ambient light signal.

In accordance with the disclosed embodiments, the controller 130 is configured to iteratively vary the size of tsep until the digital value received from the ADC 126 during the first ambient sense phase is within a threshold of the digital value received during the second ambient sense phase. The digital values used for the comparison could be the average values taken over multiple cycles. In some embodiments, the controller iteratively increases the size of tsep until VA approximately equals VA'. An example of this result is illustrated in FIG. 3. The plot of FIG. 3 is similar to that of FIG. 2 but tsep has been increased to the point at which VA approximately equals VA'. With the light source sense phase 152 separated from the first ambient sense phase 162 by a tsep time period that approximately equals the period of the ambient light signal 150, then the magnitude of the measured ambient signal (VA) measured during the ambient sense phase 162 approximately equals the magnitude of the ambient light signal incident on the photodetector 122 during the light source sense phase 152. The measured ambient light value VA can be subtracted from the measured light signal during the light source sense phase (VL) to generate a sufficiently accurate value for the magnitude of the light reflected off the person from just the LED 112. Any bio-physical calculation made using this latter value will not be based on much or any ambient light and thus be more accurate than if the ambient light were not factored out of the measurements and calculations.

Figure 4:
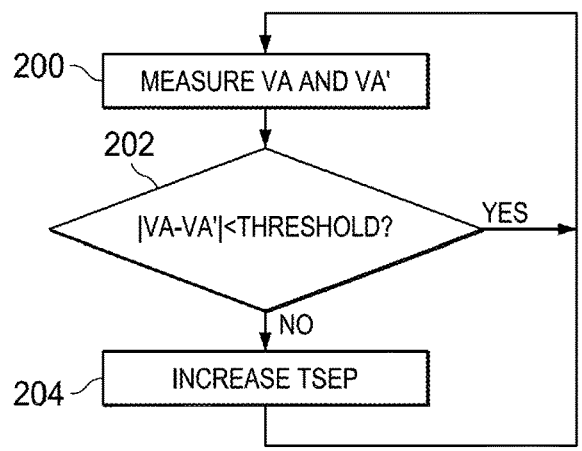
FIG. 4 shows a method in accordance with various examples.

FIG. 4 illustrates a method in accordance with various embodiments. At 200, the method includes measuring VA and VA' for a particular setting for tsep. The value of tsep may be set to a default value implemented by the controller 130. The controller 130 reads a first digital value from the ADC (VA) and, after the time tsep, a second digital value (VA'). The controller may read multiple pairs of VA and VA' values from the ADC 136 and average together the VA values to produce an average VA value and average together the VA' values to produce an average VA' value.

At 202, the controller 130 then computes the difference between the VA and VA' values (or the averaged values) and determines whether the difference is less than a threshold. The threshold is configured in the controller 130. The threshold is relatively small and represents a value below the difference between VA and VA' is considered small enough such that VA and VA' are determined to be substantially equal. When VA and VA' are substantially equal, the value of tsep represents the period of the underlying ambient light signal. In the example of FIG. 4, the absolute value of the difference between VA and VA' is compared to the threshold. In other embodiments, the controller 130 computes the square of the difference between VA and VA' and compares the square of the difference to a threshold.

If the difference between VA and VA' (its absolute value, the square of the difference, etc.) is greater than the threshold, then at 204, the controller 204 increases the size of tsep and control loops back to 200 and the process repeats. The process iterates until the difference between VA and VA' is less than threshold at which time the value of tsep approximates the period of the ambient light signal. That value of tsep is used to compute the biophysical parameter through acquisition of a digital value during a light source sense phase and a digital value from an ambient sense phase a tsep period of time following the light source sense phase. In some embodiments, the ambient sense phase is an integer multiple of tsep values following the light source sense phase.

Figure 5:
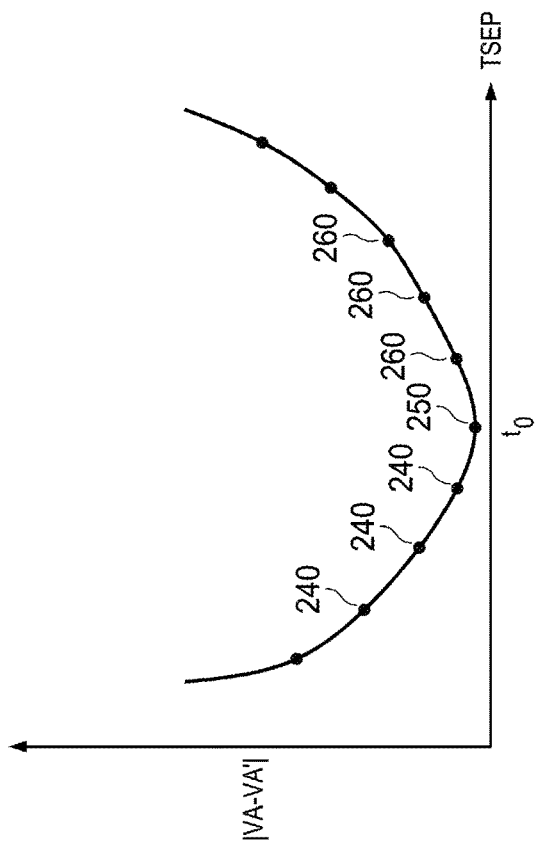
FIG. 5 illustrates the relationship between the difference between successive ambient light samples and the time period separating the ambient light samples.

FIG. 5 illustrates the relationship between the difference between successive ambient light samples (VA and VA') separated by varying values of tsep. The difference between VA and VA' is illustrated in FIG. 5 as the absolute value of the difference, but an alternative representation could include the square of the difference. At a particular value of tsep ($t_0$), the difference between VA and VA' is a minimum as shown. The method of FIG. 4 includes determining at 202 whether the difference value is less than the threshold. In some embodiments, the method may include sweeping the value of tsep from a higher value to a lower value, or vice versa and determining the value of tsep for which the difference value (VA-VA') is the lowest. In some embodiments, each measurement of VA and VA' for a given value of tsep includes multiple measurements that are averaged together by the controller 130 as explained above.

In some embodiments to be less susceptible to noise, the controller may determine the value of tsep as $t_0$ by determining the value of tsep for which the neighboring difference values on either side are greater than the difference value at a given tsep. In some embodiments, the controller determines the value of tsep for which n neighboring difference values are greater than the difference value at a given tsep. The value of n may be, for example, 6 meaning that 6 neighboring difference values (e.g., the three values 240 and the three values 260) must be greater than the value 250 for the tsep value corresponding to 250 to be determined to be the value of tsep to be used for the subsequent biophysical measurements.

Figure 6:
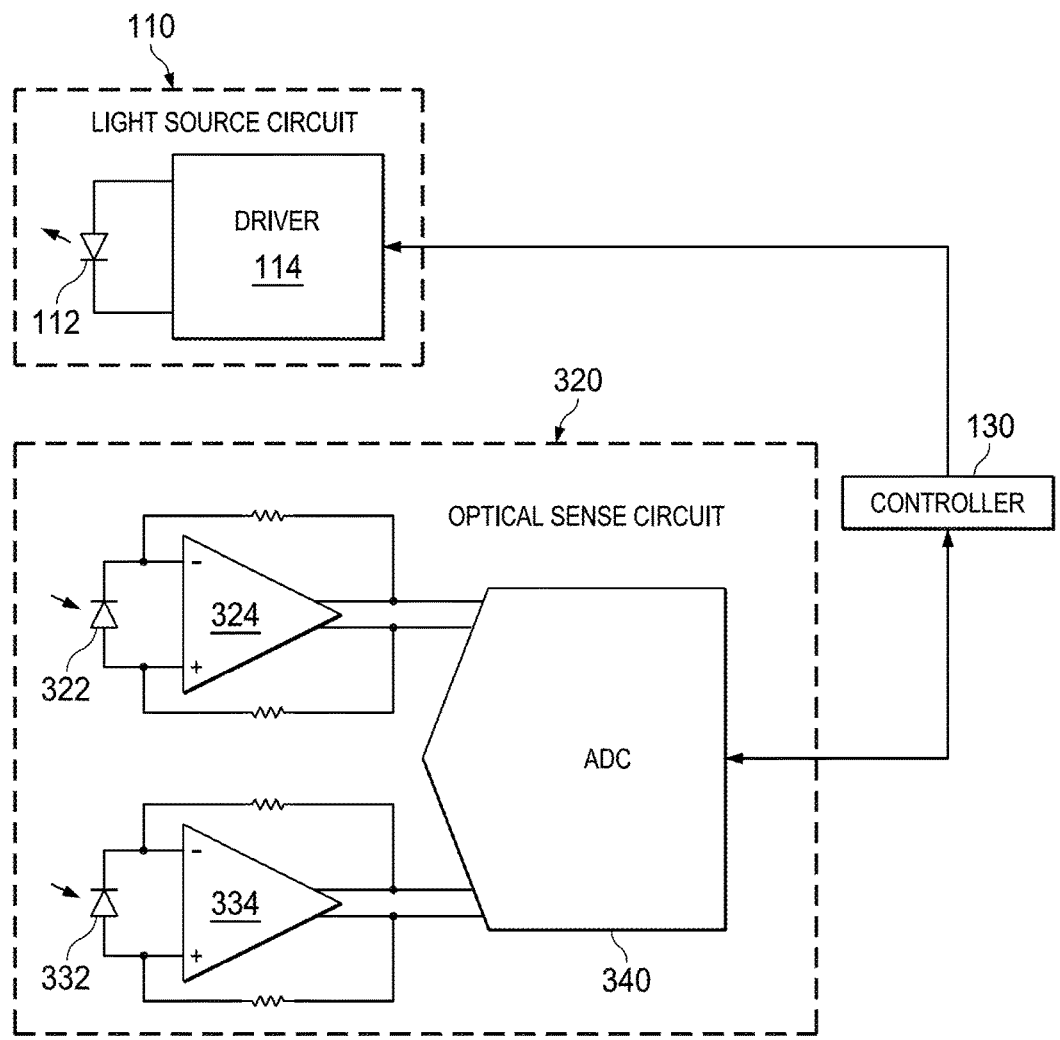
FIG. 6 illustrates a block diagram of an optical bio-sensing device in accordance with an alternative embodiment.

In some embodiments, an optical bio-sensing device has multiple photodiodes, with one photodiode being used for calibration purposes to calibrate the value of tsep and the other photodiode used to measure the biophysical parameter. FIG. 6, for example, shows an embodiment of a bio-sensing device including a light source circuit 110 (including an LED 112 and driver 114 as described above), a controller 130 and an alternative optical sense circuit 320 from that shown in FIG. 1. The optical sense circuit 320 in FIG. 6 includes a pair of photodiodes 322 and 332. Each photodiode is coupled to a corresponding transimpedance amplifier 324, 334. The current generated from photodiode 322 is converted to an analog voltage by transimpedance amplifier 324 and the current generated from photodiode 332 is converted to an analog voltage by transimpedance amplifier 334. The analog voltage representations of photodiode current are provided to an ADC 340. The ADC 340 may be a multi-channel ADC and thus be capable of digitizing individual analog inputs such as inputs from the transimpedance amplifiers 324 and 334. Other implementations may include separate ADCs rather than one multi-channel ADC. Further still, a single transimpedance amplifier could be used for the two photodiodes 322, 332. The controller 130 can read digital values from the ADC 340 for either of the photodiodes.

Figure 7:
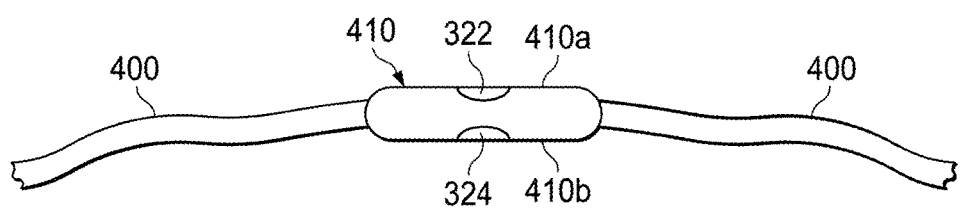
FIG. 7 illustrates an embodiment of the optical bio-sensing device as a wrist-worn device with photodiodes on opposing surfaces of a housing of the device.

In one embodiment as noted above, the bio-sensing device is implemented in the form of a wrist-worn device similar to a watch, and may include a time function like a watch. FIG. 7 shows an example of such an embodiment, the device includes a wrist-worn band 400 and a housing 410 containing the light source (e.g., photodiode 122, 322, 332), the transimpedance amplifier (124, 324, 334), the ADC (126, 340), and other components of the device not shown (e.g., display, battery, etc.). The housing 410 may comprise metal, plastic or other suitable material and have opposing surfaces 410a and 410b. Surface 410b rests adjacent the person's skin when the watch is strapped to the person's wrist. Surface 410a is opposite surface 410a and thus on the side of the device opposite the wrist.

The photodiode 324 of FIG. 6 is provided on surface 410b and the photodiode 322 is provided on surface 410a. Each photodiode may be mounted within the housing 410 may be exposed to the outside of the housing through a suitably sized aperture. The photodiode adjacent the person's wrist is the photodiode used by the controller to measure the biophysical parameter. In the example of FIG. 7, that measurement photodiode is photodiode 324. Because photodiode 324 is in direct or near direct contact with the person's wrist, not much ambient light is received into that photodiode. However, enough ambient light may be received into the measurement photodiode that the controller in the device needs to perform ambient sense phases to subtract out the ambient light signal from the light source sensing phases as explained above. However, due to the geometry of the watch relative to the person's wrist, the tightness with which the person wears the device on his or her wrist, the amount of ambient light received by photodiode 324 may be variable and may affect the quality of the ambient signal for purposes of computing tsep to approximate the period of the periodic ambient light signal.

Because the photodiode 322 is positioned opposite the person's wrist and thus directly exposed to the ambient light, that photodiode provides better performance for measuring the period of the ambient light. Thus, in the embodiment of FIGS. 6 and 7, photodiode 322 is used to acquire and compare the values of VA and VA' as explained above. Once the value of tsep is determined so as to approximate the period of the ambient light signal, that value of tsep is used to make biophysical parameter measurements. That is, the controller 130 reads a digital value from the ADC 340 during a light source sense phase for photodiode 324 and then reads another digital value from the ADC also for photodiode 324 during an ambient sense phase spaced apart from the light source sense phase by an integer multiple of tsep, where tsep was determined using the photodiode 322.

In some embodiments, the device performs the calibration technique described herein upon power-on and/or at discrete intervals during operation (e.g., once every minute, every 5 minutes, etc.). The disclosed calibration techniques render the resulting computed bio-physical parameter more accurate.

In some examples, controller 130 may determine (or estimate) a value indicative of an integer multiple of a period of ambient light based on one or more ambient light measurements, and control a time interval (or time period) between a light source-enabled measurement and a first ambient measurement (i.e., a light source-disabled measurement) based on the determined value. The first ambient measurement may be used to cancel ambient light from the light-source enabled measurement. In some examples, controller 130 may determine the value indicative of the integer multiple of the period of the ambient light phase by adjusting the time interval between two or more successive ambient light measurements such that the successive ambient light measurements are approximately equal.

In some examples, controller 130 may use a single light detector (e.g., a photodiode) to perform the successive ambient light measurements, the first ambient light measurement, and the light source-enabled measurements. In further examples, controller 130 may use separate light detectors (e.g., photodiodes) to perform the successive ambient light measurements and the light source-enabled measurements. For example, controller 130 may use a first light detector on a first face of a device that is proximate to the skin of a user of the device to perform the light source-enabled measurement and the first ambient light measurement, and use a second light detector on a second face of the device to perform the successive ambient light measurements (for determining the time interval between the light source-enabled measurement and the first ambient light measurement). In some examples, the second face of the device may be opposite the first face of the device. In further examples, the exposure of the second face of the device to ambient light may be greater than the exposure of the first face of the device to ambient light. In additional examples, the second face of the device may be facing a direction that is opposite the skin of a user of the device.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A bio-sensing device, comprising:
 a light source circuit;
 a first photodetector;
 a transimpedance amplifier coupled to the first photodetector and configured to convert a current produced by the photodetector to a voltage;
 an analog-to-digital converter (ADC) coupled to the transimpedance amplifier and configured to convert the voltage from the first photodetector to a digital value; and
 a controller coupled to the ADC and the light source circuit and configured to:
  initiate a light source sense phase followed by a first ambient sense phase and a second ambient sense phase, wherein in the light source sense phase, the controller is configured to receive a digital value from the ADC while the light source circuit is enabled and wherein in each of the first and second ambient sense phases, the controller is configured to receive a digital value from the ADC while the light source circuit is disabled, wherein a first time period between the light source sense phase and the first ambient sense phase is equal to a second time period between the first and second ambient sense phases; and
  iteratively vary the second time period, while maintaining the first and second time periods equal, until the digital value received during the first ambient sense phase is within a threshold of the digital value received during the second ambient sense phase.

2. The bio-sensing device of claim 1, wherein the optical sense circuit includes a single photodetector.

3. The bio-sensing device of claim 1, wherein the optical sense circuit includes a first photodetector and a second photodetector.

4. The bio-sensing device of claim 3, further comprising a wrist-worn band and a housing containing the light source circuit, the transimpedance amplifier, the ADC, and the controller, wherein the housing includes first and second surfaces, the first surface configured to be placed against a person's wrist and the second surface opposite the first surface, and wherein the first photodetector is positioned on the first surface and the second photodetector is positioned on the second surface.

5. The bio-sensing device of claim 1, wherein the controller is configured to determine whether the digital value received during the first ambient sense phase is within the threshold of the digital value received during the second ambient sense phase through computation by the controller of a difference between the digital values received during the first and second ambient sense phases.

6. The bio-sensing device of claim 5, wherein the controller is configured to compute a square of the difference.

7. The bio-sensing device of claim 5, wherein the controller is configured to compute an absolute value of the difference.

8. The bio-sensing device of claim 5, wherein the controller is configured to read a plurality of digital values from the ADC during through multiple sets of first and second ambient sense phases and compute an average of the differences of the digital values read during each first ambient sense phase and corresponding second ambient sense phase.

9. The bio-sensing device of claim 1, wherein the controller is configured to determine at least one of a heart rate value, a peripheral oxygen saturation value, and a pulse transit time.

10. A system, comprising:
 a first photodetector coupled to a first transimpedance amplifier and configured to convert a current produced by the first photodetector to a voltage;
 a second photodetector coupled to a second transimpedance amplifier and configured to convert a current produced by the second photodetector to a voltage;
 an analog-to-digital converter (ADC) configured to convert voltages from the first and second transimpedance amplifiers to corresponding digital values; and
 a controller coupled to the ADC and configured to:
  iteratively read digital values from the ADC generated from the second photodetector while a light source is disabled during a plurality of sets of first and second ambient sense phases, wherein the first ambient sense phase is separated from the second ambient sense phase of a given set by a variable time separation, the time separation adjusted for each subsequent set of first and second ambient sense phases;
  compute a difference between the digital values read during each set of ambient sense phases;
  determine the approximate period of the ambient light from processing the computed differences; and
  using the determined approximate ambient light period, configure a time separation between a light source sense phase in which the light source is enabled and an ambient sense phase in which the light source is disabled.

11. The system of claim 10, wherein the controller is configured to compute a biophysical parameter of a person using digital values read from the ADC during light source and ambient sense phases separated by the configured time period.

12. The system of claim 10, further comprising a wrist-worn band and a housing containing the light source circuit, the first and second transimpedance amplifiers, the ADC, and the controller, wherein the housing includes first and second surfaces, the first surface configured to be placed against a person's wrist and the second surface opposite the first surface, and wherein the first photodetector is positioned on the first surface and the second photodetector is positioned on the second surface.

13. The system of claim 10, wherein the controller is configured to approximate the period of the ambient light through determination of the adjusted time period corresponding to a minimum computed difference.

14. The system of claim 13, wherein the controller is configured to configure the time period to be an integer multiple of the approximated period of the ambient light.

15. The system of claim 10, wherein the light source circuit includes a light emitting diode (LED).

16. A method of calibrating a bio-sensing device, comprising:
- performing a plurality of iterations, each iteration including measuring a magnitude of ambient light during a first ambient light phase with a light source in the bio-sensing device turned off, after a configurable time delay measuring the magnitude of ambient light during a second ambient light phase also with the light source turned off, determining that a difference between the measured magnitudes is greater than a threshold, and adjusting the configurable time delay,
- performing the plurality of iterations until the difference is less than the threshold to compute a measurement time period based on the difference, and
- configuring the bio-sensing device to obtain measurements separated by a time interval based on the measurement time period.

17. The method of claim 16, further comprising computing a bio-physical parameter using measurements of ambient light and reflected light off a person generated by a light source in the bio-sensing device, wherein the measurements are separated by the time interval based on the measurement time period.

18. The method of claim 17, wherein time interval is an integer multiple of the measurement time period.

19. The method of claim 16, wherein determining that the difference is greater than the threshold comprising computing an absolute value or a square of the difference.

* * * * *